US00PP28590P2

(12) United States Plant Patent
Sato et al.

(10) Patent No.: US PP28,590 P2
(45) Date of Patent: Oct. 31, 2017

(54) **NEW GUINEA *IMPATIENS* PLANT NAMED 'SAKIMP039'**

(50) Latin Name: ***Impatiens×hybrida* hort**
Varietal Denomination: SAKIMP039

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,103

(22) Filed: Mar. 30, 2016

(51) Int. Cl.
*A01H 5/02* (2006.01)

(52) U.S. Cl.
USPC ..... Plt./318.7

(58) Field of Classification Search
USPC ..... Plt./318.7
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *Impatiens* plant particularly distinguished by having red flowers with red-purple eyes, and a compact plant habit, is disclosed.

2 Drawing Sheets

Genus and species: *Impatiens×hybrida* hort.
Variety denomination: 'SAKIMP039'.

BACKGROUND OF THE NEW PLANT

The present invention comprises a new and distinct variety of New Guinea *impatiens* plant, botanically known as *Impatiens×hybrida* hort, and referred to by the variety name 'SAKIMP039'. 'SAKIMP039' originated from an interspecific hybridization in Misato, Japan between the proprietary female *Impatiens* line 'NH-248-13H' (unpatented) and the proprietary male *Impatiens* line 'NH-312-36KH' (unpatented).

In June 2011, the parental lines were crossed and a population of F1 plants was created. The F1 plants were evaluated in Misato, Japan in an open-field trial. The criteria for plant selection included deep flower color and vigorous rooting. At the completion of the trial, one single plant selection designated 'M2013-191' was made based on the above criteria and vegetatively propagated. From June to August 2013, the selection was evaluated in an open-field in Misato, Japan. Shoot-tip cuttings of the variety were then shipped to Salinas, Calif., where the plants were regenerated and re-evaluated for stability of traits. The selection, subsequently named 'SAKIMP039', was found to reproduce true to type in successive generations of asexual propagation via shoot-tip cuttings in Salinas, Calif.

SUMMARY

The following are the most outstanding and distinguishing characteristics of this new variety when grown under normal horticultural practices in Salinas, Calif.

1. Red flowers with red-purple eyes; and
2. A compact plant habit.

DESCRIPTION OF THE PHOTOGRAPHS

This *impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
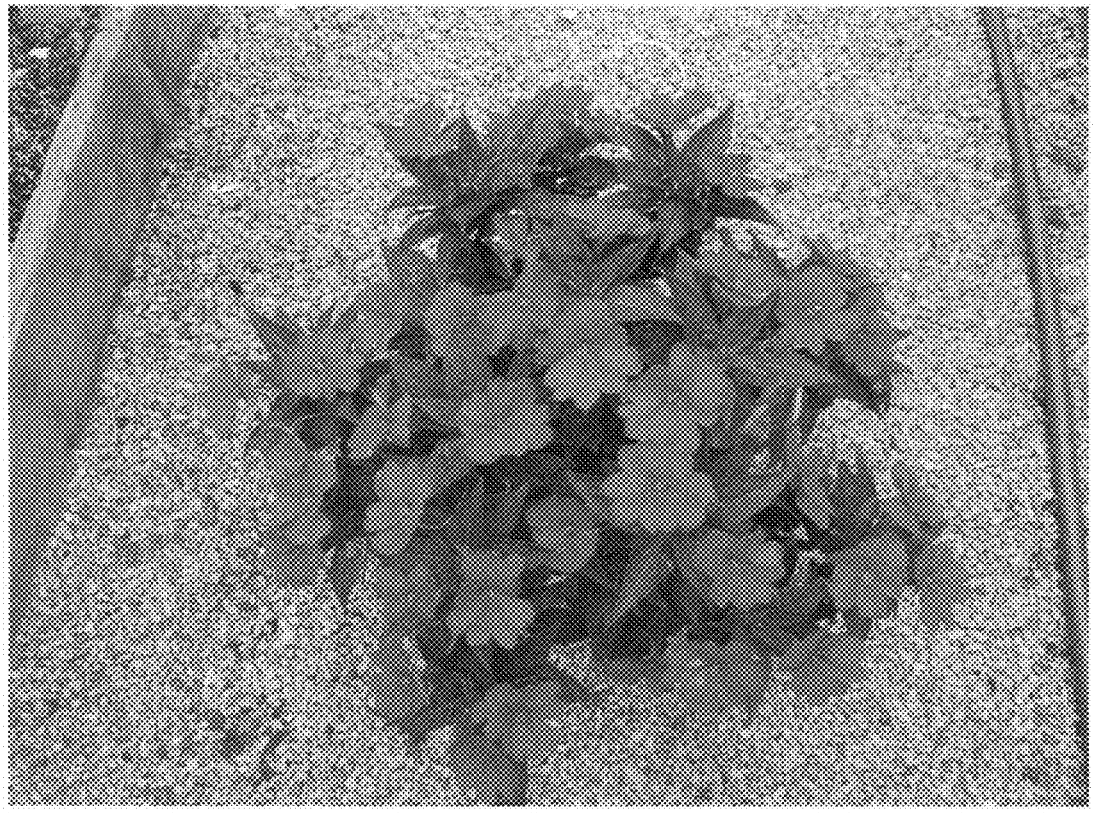
FIG. 1 shows the overall plant habit of the plant grown in a pot.
Figure 2:
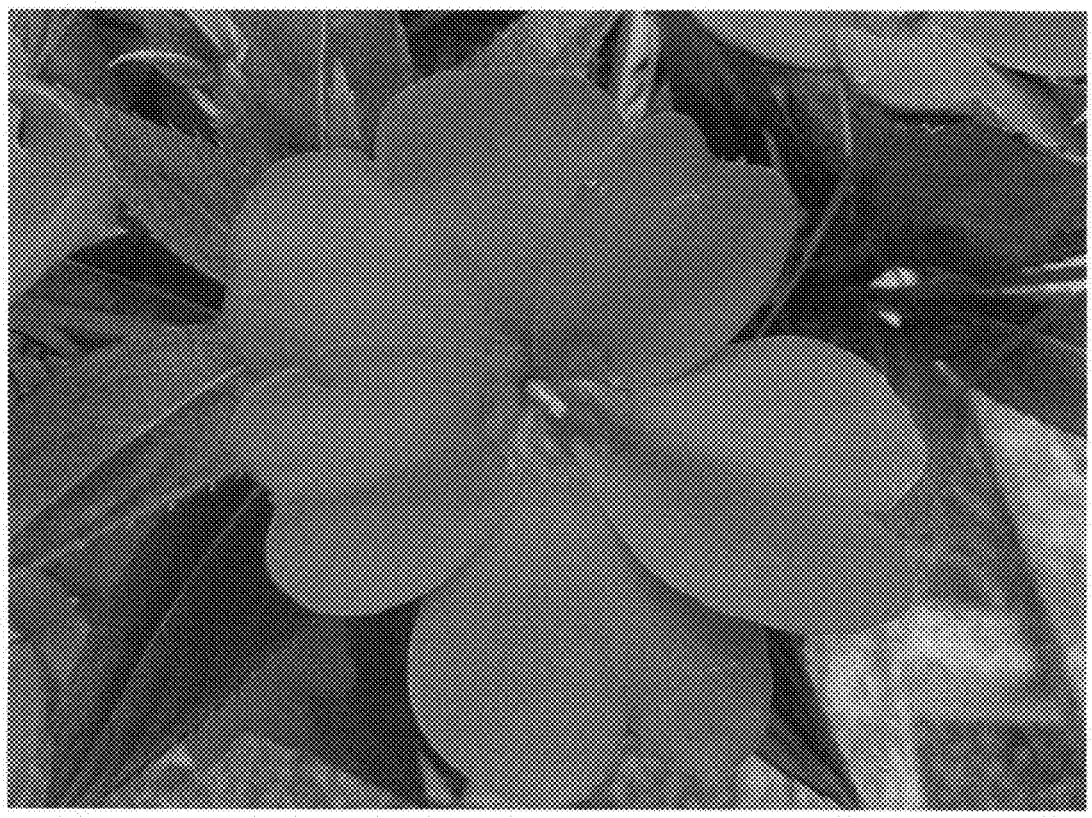
FIG. 2 shows a close-up of the mature inflorescence of the plant.

The following detailed descriptions set forth the distinctive characteristics of 'SAKIMP039'. Color references are to The Royal Horticultural Society of London Colour Chart (R.H.S.), 4$^{th}$ edition (2001). Data was collected from plants grown about 7 months from propagation by terminal cuttings in Salinas, Calif. under greenhouse conditions. Anatomic labels are from *The Cambridge Illustrated Glossary of Botanical Terms*, by M. Hickey and C. King, Cambridge University Press.

Classification:

*Family*.—Balsaminaceae.
*Botanical*.—*Impatiens×hybrida* hort.
*Common*.—*Impatiens*.
*Designation*.—'SAKIMP039'.

Growth:

*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Parentage:

*Female parent*.—The proprietary *Impatiens* variety 'NH-248-13H'.

*Male parent*.—The proprietary *Impatiens* variety 'NH-312-36KH'.

Plant:

*Habit*.—Compact.

*Height*.—29.0 cm from the soil line to the top of the foliage.

*Spread*.—44.0 cm.

*Number of branches per plant*.—14 total with 8 main branches.

*Length of branches*.—2.0 cm from the soil line to the first node, 10.0 cm total.

*Diameter of branches*.—2.5 cm for the main branch, 1.0 cm to 1.5 cm for the other secondary branches.

*Color of the branches*.—RHS 59A (Red-purple) with slight RHS 144B (Yellow-green).

*Life cycle*.—Annual.

*Time to produce a rooted cutting*.—About 4 weeks.

*Time to bloom from propagation*.—6 to 8 weeks.

*Flowering requirements*.—Will flower so long as the temperature is above 5° C.

*Temperature tolerances*.—Plants observed to continue flowering in a temperature range of 5° C. to 36° C.

Stems:

*Color*.—RHS 59A (Red-purple) with slight RHS 144B (Yellow-green).

*Anthocyanin color*.—RHS 59A (Red-purple).

*Pubescence*.—Absent.

*Description*.—Strong; circular in cross-section, smooth and shiny.

*Length*.—5.0 cm to 8.0 cm from the first to the second node; 10.0 cm to 11.0 cm total.

*Diameter*.—5.0 mm to 6.0 mm.

*Internode length*.—5.0 cm; 3.5 cm to 5.0 cm from the first node to the second node.

Leaves:

*Arrangement*.—Whorled with up to 5 leaves per node; opposite if only two leaves at one node.

*Shape*.—Lanceolate, curled.

*Apex*.—Acuminate.

*Base*.—Shortly attenuate.

*Margin*.—Serrate.

*Surface appearance*.—Dull and waxy.

*Length*.—6.5 cm.

*Width*.—2.3 cm.

*Color*.—Upper surface: RHS 139A (Yellow-green). Lower surface: RHS 138A (Green).

*Variegation*.—Absent.

*Fragrance*.—Absent.

*Surface texture*.—No pubescence.

*Petiole*.—Length: 8.0 mm. Diameter: 3.0 mm. Color: Closest to RHS 145D (Yellow-green). Surface texture: Smooth, glabrous.

*Venation pattern*.—Pinnate.

*Venation color* (*both upper and lower surfaces*).—Closest to RHS 145C (Yellow-green).

Flowers:

*Number of flowers per node*.—1 to 3 in bloom at one time; about 10 flower buds.

*Number of flower buds per plant*.—Approximately 50 to 60 in bloom.

*Lastingness of individual blooms on the plant*.—14 days.

*Flower type*.—Single with spur.

*Fragrance*.—Absent.

Corolla:

*Shape*.—Roughly circular with 5 radial petals.

*Diameter*.—5.0 cm.

*Depth*.—1.0 cm.

*Petals*.—Surface texture (both surfaces): Glabrous. Length: 2.7 cm. Width: 2.2 cm. Shape: Obcordate. Apex: Emarginate (cleaved). Margin: Entire. Base: Attenuate. Color: Upper surface: Closest to RHS 46A (Red). Lower surface: Closest to but brighter than RHS 63A (Red-purple). Eye zone: RHS 61A (Red-purple).

Calyx:

*Sepal shape*.—Lanceolate.

*Sepal number per flower*.—2.

*Sepal color*.—Upper surface: RHS 60A (Red-purple) with slight RHS 144B (Yellow-green) at the tip. Lower surface: RHS 60A (Red-purple) with slight RHS 142D (Yellow-green).

*Sepal length*.—1.0 cm.

*Sepal diameter*.—4.0 mm.

*Sepal base*.—Subcordate.

*Sepal apex*.—Caudate.

*Sepal margin*.—Entire.

*Sepal texture* (*both surfaces*).—Glabrous.

Bud:

*Surface texture*.—Glabrous.

*Length*.—1.6 cm.

*Diameter*.—1.0 cm.

*Shape*.—Deltoid longitudinal cross-section.

*Color*.—Closest to but brighter than RHS 60A (Red-purple).

Peduncle:

*Length*.—2.5 cm.

*Diameter*.—1.0 mm to 1.5 mm.

*Color*.—RHS 60A (Red-purple) with slight RHS 144C (Yellow-green).

*Surface texture*.—Smooth, glabrous.

Spur:

*Color*.—RHS 58A (Red-purple).

*Shape*.—Tubular; curved downward.

*Length*.—1.0 mm to 2.0 mm.

*Diameter*.—1.0 mm to 2.0 mm.

Reproductive organs:

*Stamen form*.—Fused; split into 4 lobes.

*Stamen number*.—5.

*Filament form*.—Free.

*Anther length*.—4.0 mm.

*Anther color*.—Closest to RHS 60A (Red-purple).

*Pistil number*.—1.

*Stigma color*.—RHS 59A (Red-purple).

*Style color*.—RHS 144A (Yellow-green).

*Ovary arrangement*.—Parietal.

*Ovary surface color*.—Closest to RHS 145B (Yellow-green).

*Pollen amount*.—Abundant.

*Pollen description*.—Powdery.

*Seed production*.—Not observed.

Disease and insect resistance: No particular resistance or susceptibility observed.

COMPARISON WITH PARENTAL LINES AND COMMERCIAL VARIETY

'SAKIMP039' is distinguished from its parents as shown in Table 1 below:

TABLE 1

| Comparison with Parental Lines | | | |
|---|---|---|---|
| Characteristic | 'SAKIMP039' | Female Parent 'NH-248-1311' | Male Parent 'NH-312-36M1' |
| Flower color | Red with Red-purple eyes | Orange | Dark red |
| Plant growth habit | Compact | Compact | Vigorous |

When 'SAKIMP039' compared to the commercial *Impatiens* variety 'SAKIMP030' (U.S. Plant Pat. No. 25,015), the following differences as described in Table 2 below.

TABLE 2

| Comparison with Similar Variety | | |
|---|---|---|
| Characteristic | 'SAKIMP039' | 'SAKIMP030' |
| Petal color, upper surface | Closest to RHS 46A (Red) | Closest to but darker than RHS 45A (Red) |
| Spur color | Closest to but brighter than RHS 58A (Red-purple) | RHS 61B (Red-purple) |
| Mature leaf color, upper surface | RHS 139A (Yellow-green) | Darker than RHS 147A (Yellow-green) |

We claim:

1. A new and distinct variety of New Guinea *Impatiens* plant named 'SAKIMP039' as described and illustrated herein.

* * * * *